(12) United States Patent
Bastide et al.

(10) Patent No.: US 11,138,714 B2
(45) Date of Patent: Oct. 5, 2021

(54) AUGMENTED REALITY PATTERN OVERLAYS TO FACILITATE WASTE REDUCTION

(71) Applicant: International Business Machines Corporation, Armonk, NY (US)

(72) Inventors: Paul R. Bastide, Ashland, MA (US); Kathleen Francis, Cambridge, MA (US); Steven Lenker, Cambridge, MA (US); Xiaoyan Wang, Boston, MA (US)

(73) Assignee: International Business Machines Corporation, Armonk, NY (US)

( * ) Notice: Subject to any disclaimer, the term of this patent is extended or adjusted under 35 U.S.C. 154(b) by 148 days.

(21) Appl. No.: 16/560,225

(22) Filed: Sep. 4, 2019

(65) Prior Publication Data

US 2021/0065349 A1    Mar. 4, 2021

(51) Int. Cl.
*G16H 20/60* (2018.01)
*G06T 7/00* (2017.01)
*G06T 19/00* (2011.01)
*G06K 9/00* (2006.01)
*G06K 9/32* (2006.01)

(52) U.S. Cl.
CPC ........ *G06T 7/0002* (2013.01); *G06K 9/00671* (2013.01); *G06K 9/325* (2013.01); *G06T 19/006* (2013.01); *G16H 20/60* (2018.01)

(58) Field of Classification Search
CPC . G06T 7/0002; G06T 19/006; G06K 9/00671; G06K 9/325
See application file for complete search history.

(56) References Cited

U.S. PATENT DOCUMENTS

| 7,415,375 | B2 | 8/2008 | Shakman et al. |
| 9,042,596 | B2 | 5/2015 | Connor |
| 9,189,021 | B2 | 11/2015 | Jerauld |
| 2002/0047867 | A1 | 4/2002 | Mault et al. |
| 2009/0221890 | A1* | 9/2009 | Saffer ................ A61M 5/1723 600/347 |
| 2013/0267794 | A1 | 10/2013 | Fernstrom et al. |

(Continued)

OTHER PUBLICATIONS

Jiang et al., "Food Nutrition Visualization on Google Glass: Design Tradeoff and Field Evaluation," IEEE Consumer Electronics Magazine, vol. 7, No. 3, pp. 21-31, May 2018.

(Continued)

*Primary Examiner* — Sam Bhattacharya
(74) *Attorney, Agent, or Firm* — Jeffrey M. Ingalls

(57) ABSTRACT

A system detects an object being viewed through a visual recognition system, the object having an associated expiration date. The system determines a caloric content associated with the object. The system assesses caloric consumption needs of at least one consumer. The system determines a likelihood of consumption of the object by the consumer based on the caloric content of the object, the caloric consumption needs of the consumer, and the expiration date of the object. The system is displayed as a gradient on a display device as an overlay associated with the object, the gradient representing a changing likelihood of total consumption of the object by the consumer over a period of time.

20 Claims, 11 Drawing Sheets

(56) References Cited

U.S. PATENT DOCUMENTS

| | | | |
|---|---|---|---|
| 2015/0312348 A1* | 10/2015 | Lustgarten | H04L 67/12 705/14.66 |
| 2016/0035248 A1 | 2/2016 | Gibbs | |
| 2016/0063692 A1 | 3/2016 | Divakaran et al. | |
| 2017/0105081 A1* | 4/2017 | Jin | G06T 13/80 |
| 2018/0085580 A1* | 3/2018 | Perez | A61N 1/37247 |
| 2019/0272557 A1* | 9/2019 | Smith | G06F 17/18 |
| 2020/0327601 A1* | 10/2020 | Kim | F25D 29/00 |
| 2021/0035196 A1* | 2/2021 | Resheff | G06Q 30/0639 |

OTHER PUBLICATIONS

Anonymous, "Method and Apparatus to Apply Visual Analytics to Refrigerator Images to Increase Dinner Choices and Reduce Food Waste." IP.com Disclosure No. IPCOM000245337D, Pub. Date: Mar. 1, 2016, 4 pages.

Ahn et al., "Supporting Healthy Grocery Shopping via Mobile Augmented Reality." ACM Trans. Multimedia Comput. Commun. Appl., vol. 12, No. 1s, Article 16 (Oct. 2015), 24 pages.

Gunders et al., "Wasted: How America Is Losing up to 40 Percent of Its Food From Farm to Fork to Landfill", Report, NRDC, Aug. 2017, 58 pages. https://www.nrdc.org/sites/default/files/wasted-2017-report.pdf.

Osmond, "Portion Control Made Easy with New AR Menu App", VR Fitness Insider, Jun. 15, 2017, 4 pages. https://www.vrfitnessinsider.com/portion-control-kabaq-ar-menu-app/.

SugAR Poke, EChO—Eradicate Childhood Obesity Foundation, printed Jun. 5, 2019, 17 pages. https://www.sugarpoke.org/.

Dent Reality, Indoor Maps and Augmented Reality Navigation, Copyright © 2019 Dent Reality LTD, printed Jun. 5, 2019, 5 pages. https://www.dentreality.com/.

Takahashi, "IBM launches augmented reality app for grocery stores", Venture Beat, Jul. 1, 2012, 7 pages. https://venturebeat.com/2012/07/01/ibm-launches-augmented-reality-shopping-app/.

Gutierrez et al., "PHARA: a personal health augmented reality assistant to support decision-making at grocery stores", International Workshop on Health Recommender Systems, Aug. 2017, Como, Italy, 4 pages. http://ceur-ws.org/Vol-1953/healthRecSys17_paper_7.pdf.

Olio, The Food Sharing Revolution, printed Jun. 5, 2019, 5 pages. https://olioex.com/.

Bozhinova, "16 Apps Preventing Food Waste", Food Tank, © 2013-2019 Food Tank, 2 pages. https://foodtank.com/news/2018/09/apps-preventing-food-waste/.

Wong, "Tackling food waste around the world: our top 10 apps", The Guardian, Feb. 6, 2017, 4 pages. https://www.theguardian.com/sustainable-business/2017/feb/06/food-waste-apps-global-technology-leftovers-landfill.

Barcode Lookup, UPC, EAN, ISBN Search, © 2019 barcodelookup.com, printed Jun. 5, 2019, 10 pages. https://www.barcodelookup.com/.

OpenCV, "About", printed Jun. 5, 2019, © Copyright 2019, OpenCV team, 9 pages. https://opencv.org/about/.

FooDB, printed Jun. 5, 2019, 2 pages. http://foodb.ca/.

"Fruits and Vegetables Serving Sizes", American Heart Association, printed Jun. 5, 2019, 4 pages. https://www.heart.org/en/healthy-living/healthy-eating/add-color/fruits-and-vegetables-serving-sizes.

Apple Developer, "Get ready for the latest advances in augmented reality." Augmented Reality, Copyright © 2019 Apple Inc., printed Jun. 5, 2019, 3 pages. https://developer.apple.com/augmented-reality/.

"Supported Devices", ARCore, Google Developers, Last updated May 16, 2019, 7 pages. https://developers.google.com/ar/discover/supported-devices.

* cited by examiner

AUGMENTED REALITY PATTERN OVERLAYS TO FACILITATE WASTE REDUCTION

BACKGROUND

The present disclosure relates generally to the prevention of food waste, and more specifically, to utilizing an augmented reality (AR) system that determines a likelihood of consumption of products at the time of purchase, and then issues a notification to a consumer indicating a likelihood of possible food waste.

In contrast to virtual reality, in which a user is fully immersed within a virtual or simulated environment, augmented reality "augments" a real-world environment using computer-generated sensory information (e.g., visual, auditory, haptic, somatosensory and/or olfactory). The computer-generated sensory information can either add to the real-world environment (e.g., constructive) or mask aspects of the real-world environment (e.g., destructive). Augmented reality may be used to overlay or modify sensory information associated with the real-world environment, thereby enhancing the experience of a user observing the real-world environment.

SUMMARY

Embodiments of the present disclosure are directed to a method that includes detecting an object being viewed through a visual recognition system, the object having an associated expiration date. The method includes determining a caloric content associated with the object. The system assesses caloric consumption needs of at least one consumer. The method includes determining a likelihood of consumption of the object by the consumer based on the caloric content of the object, the caloric consumption needs of the consumer, and the expiration date of the object. The method includes displaying a gradient on a display device as an overlay associated with the object, the gradient representing a changing likelihood of total consumption of the object by the consumer over a period of time.

Other embodiments of the present disclosure are directed to a computer system and computer program product for performing the method.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, explain the principles of the disclosure. The drawings are only illustrative of certain embodiments and do not limit the disclosure.

DETAILED DESCRIPTION

Research indicates that a large amount of food is wasted in the United States, with a significant portion of the waste occurring in households. A portion of this wasted food is edible, and this has an associated cost for households. In addition to the immediate monetary costs associated with wasted food, there are related costs such as water, energy, greenhouse gas emissions, and other resources that are necessary for producing the food.

The embodiments described herein provide for systems, methods and computer program products that use augmented reality (AR) to alert consumers, at a point in time before purchasing food, that there is a potential for waste.

Figure 1:
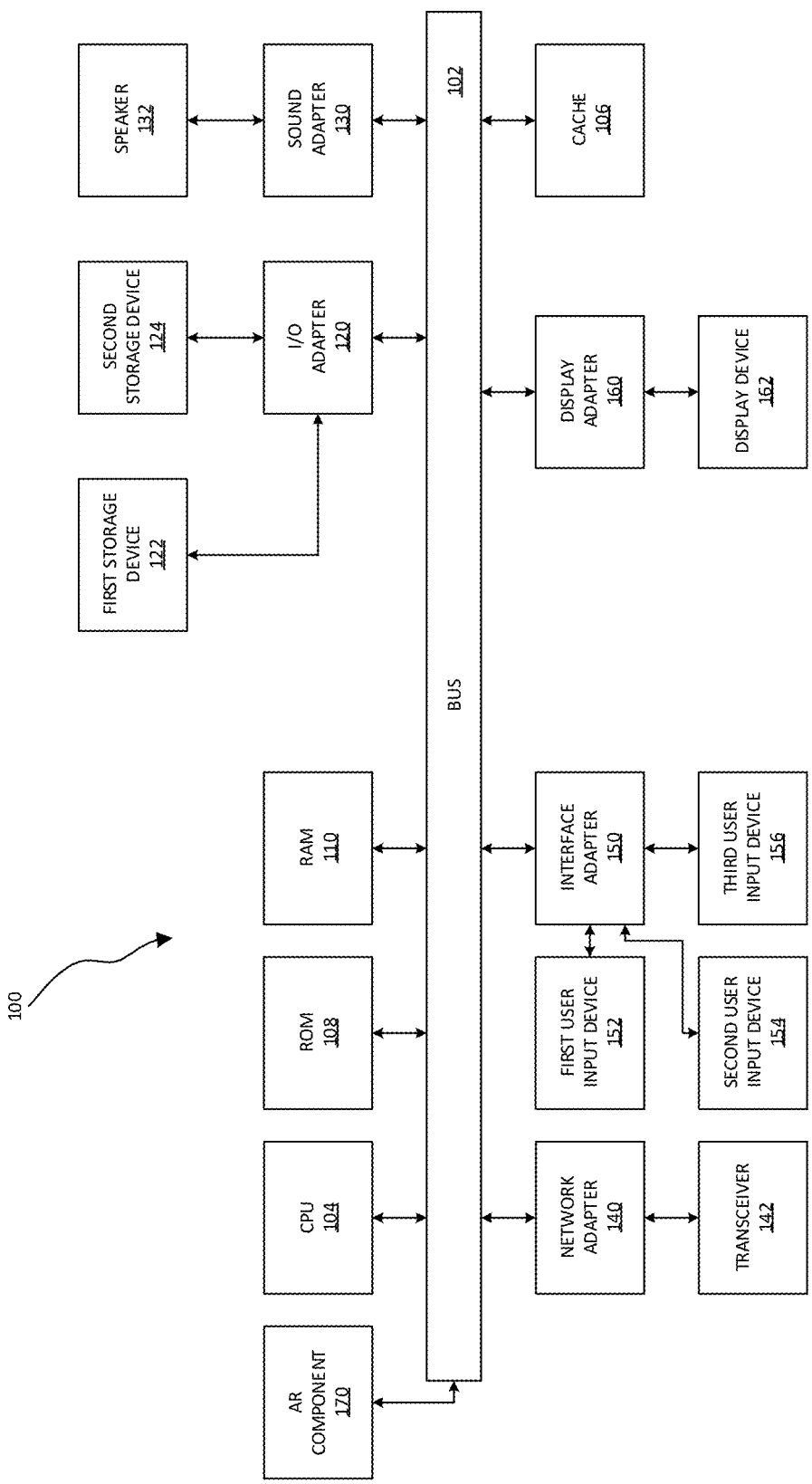
FIG. 1 depicts a block diagram of a processing system, according to embodiments.

Referring now to the drawings in which like numerals represent the same or similar elements and initially to FIG. 1, an exemplary processing system 100 to which the present embodiments may be applied is shown in accordance with one embodiment. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 may be any of a disk storage device (e.g., a magnetic or optical disk storage device), a solid-state magnetic device, and so forth. The storage devices 122 and 124 may be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 may be any of a keyboard, a mouse, a keypad, an image capture device, a motion sensing device, a microphone, a device incorporating the functionality of at least two of the preceding devices, or any other suitable types of input devices. The user input devices 152, 154, and 156 may be the same type of user input device or different types of user input devices. The user input devices 152, 154, and 156 are used to input and output information to and from system 100.

Augmented reality (AR) component 170 may be operatively coupled to system bus 102. AR component 170 is configured to communicate with an AR device worn by a user (e.g., see FIG. 4A, augmented reality display system 403) to perform one or more of the operations described below. AR component 170 may be implemented as a stand-alone special purpose hardware device (e.g., see FIG. 4A, augmented reality display system 403), or it may be implemented as software stored on a storage device. In the embodiment in which AR component 170 is software-implemented, although shown as a separate component of the computer system 100, AR component 170 may be stored on, e.g., the first storage device 122 and/or the second storage device 124. Alternatively, AR component 170 may be stored on a separate storage device (not shown).

The processing system 100 may also include other elements (not shown), as readily contemplated by one of skill in the art, as well as omit certain elements. For example, various other input devices and/or output devices may be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present disclosure provided herein.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service.

A cloud computing environment is service oriented with a focus on statelessness, low coupling, modularity, and semantic interoperability. At the heart of cloud computing is an infrastructure that includes a network of interconnected nodes.

Figure 2:
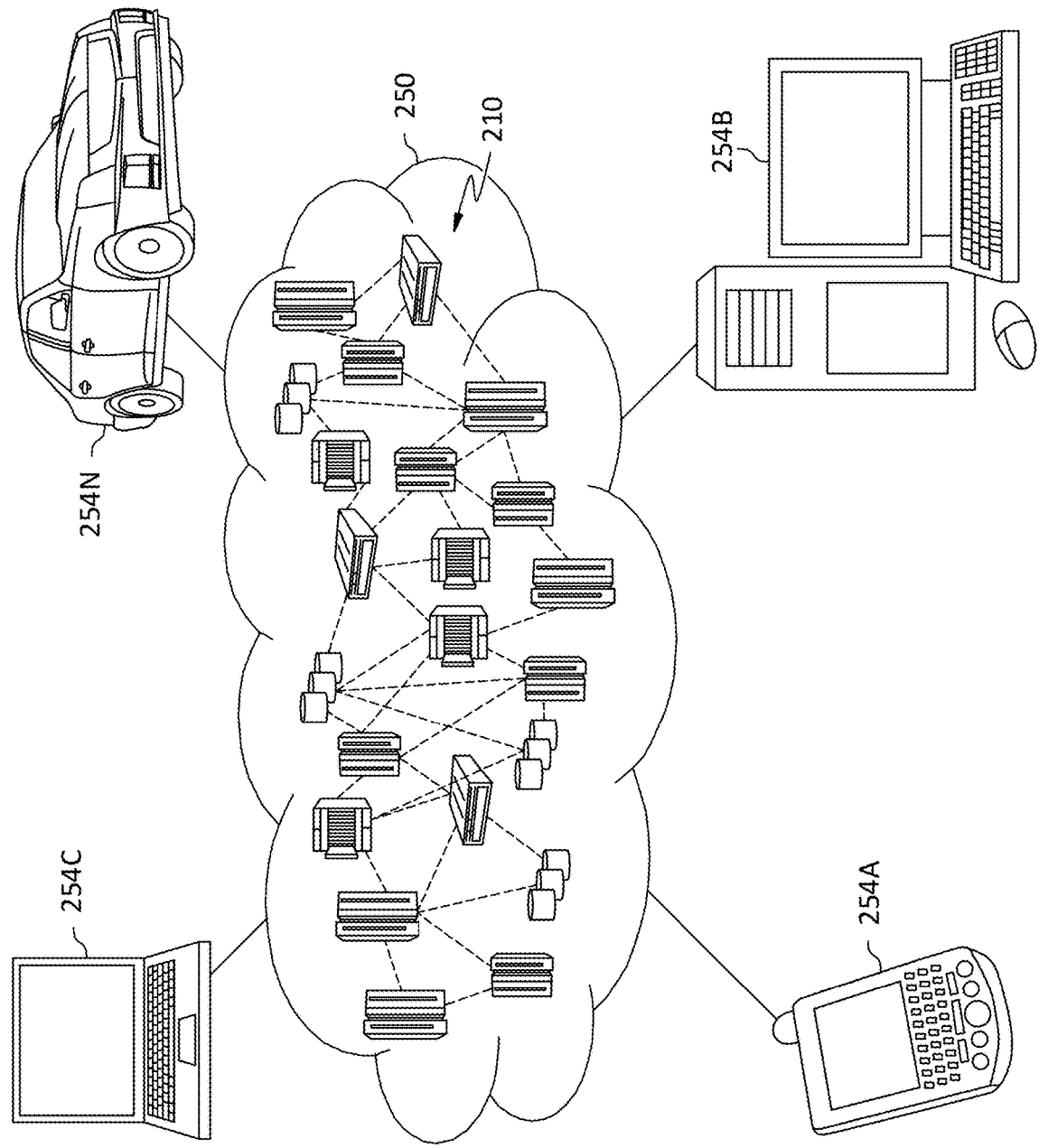
FIG. 2 is a block diagram of an illustrative cloud computing environment having one or more computing nodes with which local computing devices used by cloud customers to communicate, according to embodiments.

Referring now to FIG. 2, illustrative cloud computing environment 250 is depicted. As shown, cloud computing environment 250 includes one or more cloud computing nodes 210 with which local computing devices used by cloud consumers, such as, for example, personal digital assistant (PDA) or cellular telephone 254A, desktop computer 254B, laptop computer 254C, and/or automobile computer system 254N may communicate. Nodes 210 may communicate with one another. They may be grouped (not shown) physically or virtually, in one or more networks, such as Private, Community, Public, or Hybrid clouds as described hereinabove, or a combination thereof. This allows cloud computing environment 250 to offer infrastructure, platforms and/or software as services for which a cloud consumer does not need to maintain resources on a local computing device. It is understood that the types of computing devices 254A-N shown in FIG. 2 are intended to be illustrative only and that computing nodes 210 and cloud computing environment 250 can communicate with any type of computerized device over any type of network and/or network addressable connection (e.g., using a web browser).

Figure 3:
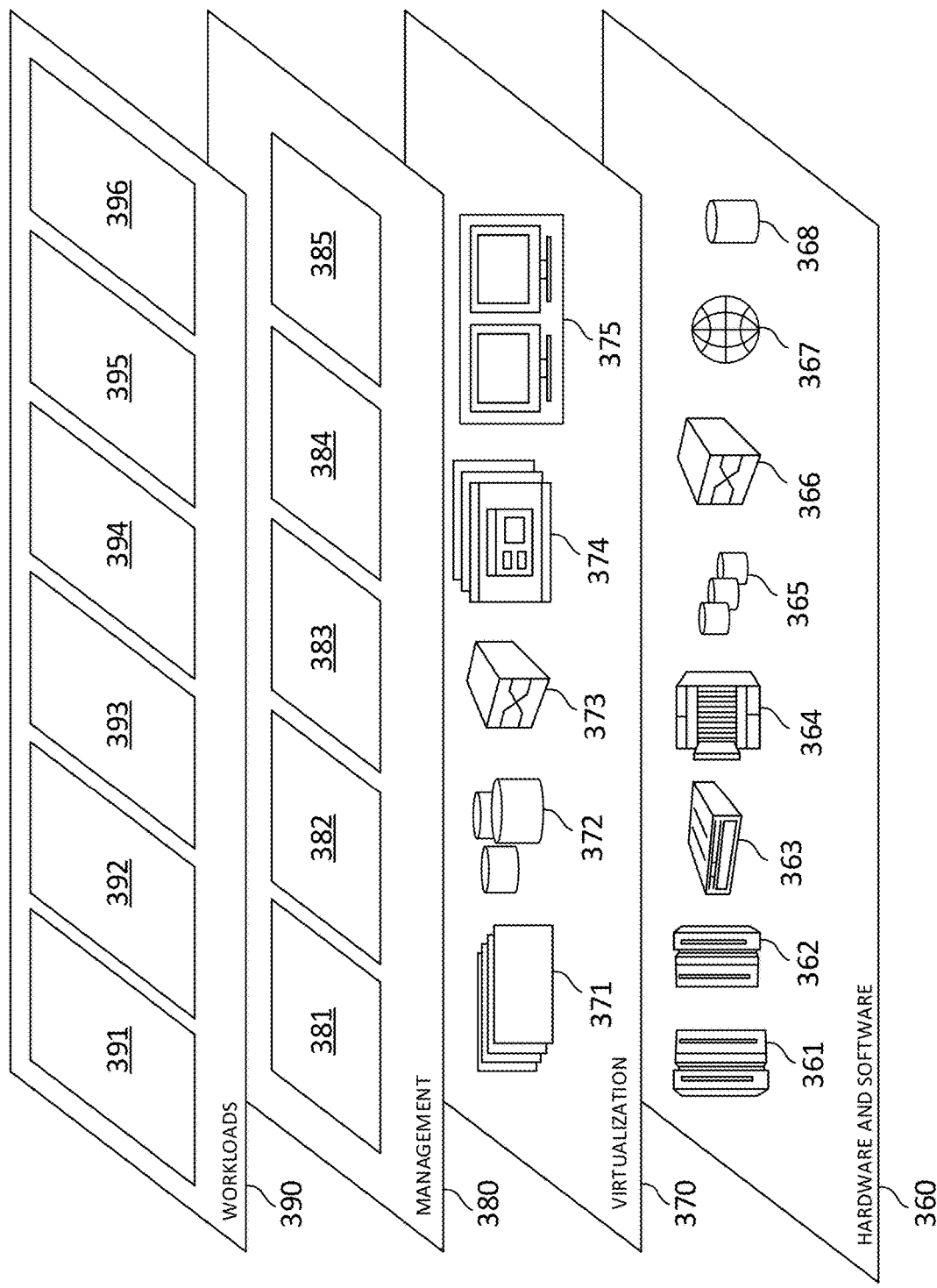
FIG. 3 is a block diagram of a set of functional abstraction layers provided by a cloud computing environment, according to embodiments.

Referring now to FIG. 3, a set of functional abstraction layers provided by cloud computing environment 250 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 360 includes hardware and software components. Examples of hardware components include: mainframes 361; RISC (Reduced Instruction Set Computer) architecture-based servers 362; servers 363; blade servers 364; storage devices 365; and networks and networking components 366. In some embodiments, software components include network application server software 367 and database software 368.

Virtualization layer 370 provides an abstraction layer from which the following examples of virtual entities may be provided: virtual servers 371; virtual storage 372; virtual networks 373, including virtual private networks; virtual applications and operating systems 374; and virtual clients 375.

In one example, management layer 380 may provide the functions described below. Resource provisioning 381 provides dynamic procurement of computing resources and other resources that are utilized to perform tasks within the cloud computing environment. Metering and Pricing 382 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 383 provides access to the cloud computing environment for consumers and system administrators. Service level management 384 provides cloud computing resource allocation and management such that required service levels are met. Service Level Agreement (SLA) planning and fulfillment 385 provide pre-arrangement for, and procurement of, cloud computing resources for which a future requirement is anticipated in accordance with an SLA.

Workloads layer 390 provides examples of functionality for which the cloud computing environment may be utilized. Examples of workloads and functions which may be provided from this layer include: mapping and navigation 391; software development and lifecycle management 392; virtual classroom education delivery 393; data analytics processing 394; transaction processing 395; and augmented reality 396.

Figure 4A:
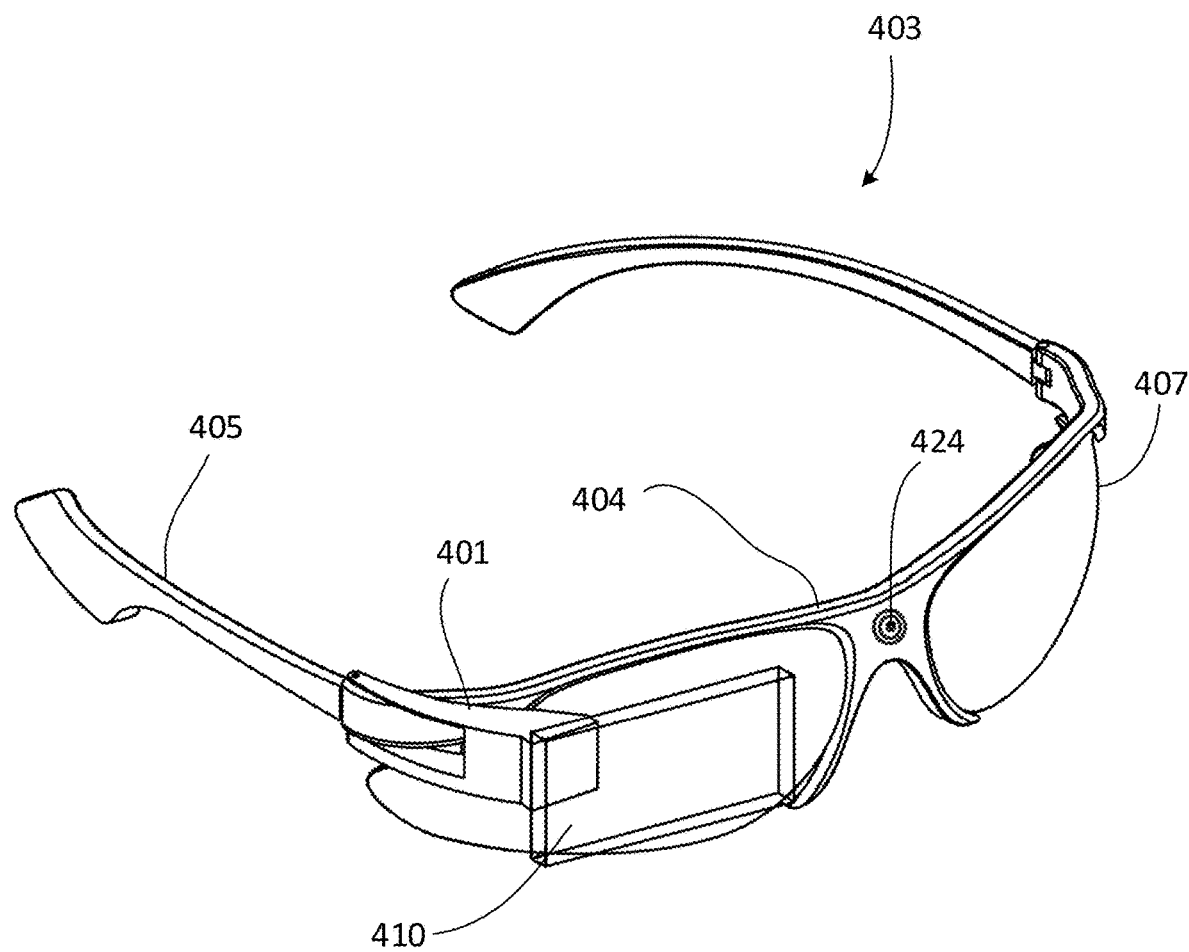
FIG. 4A depicts an isometric view of an augmented display system, according to an embodiment.
Figure 4B:
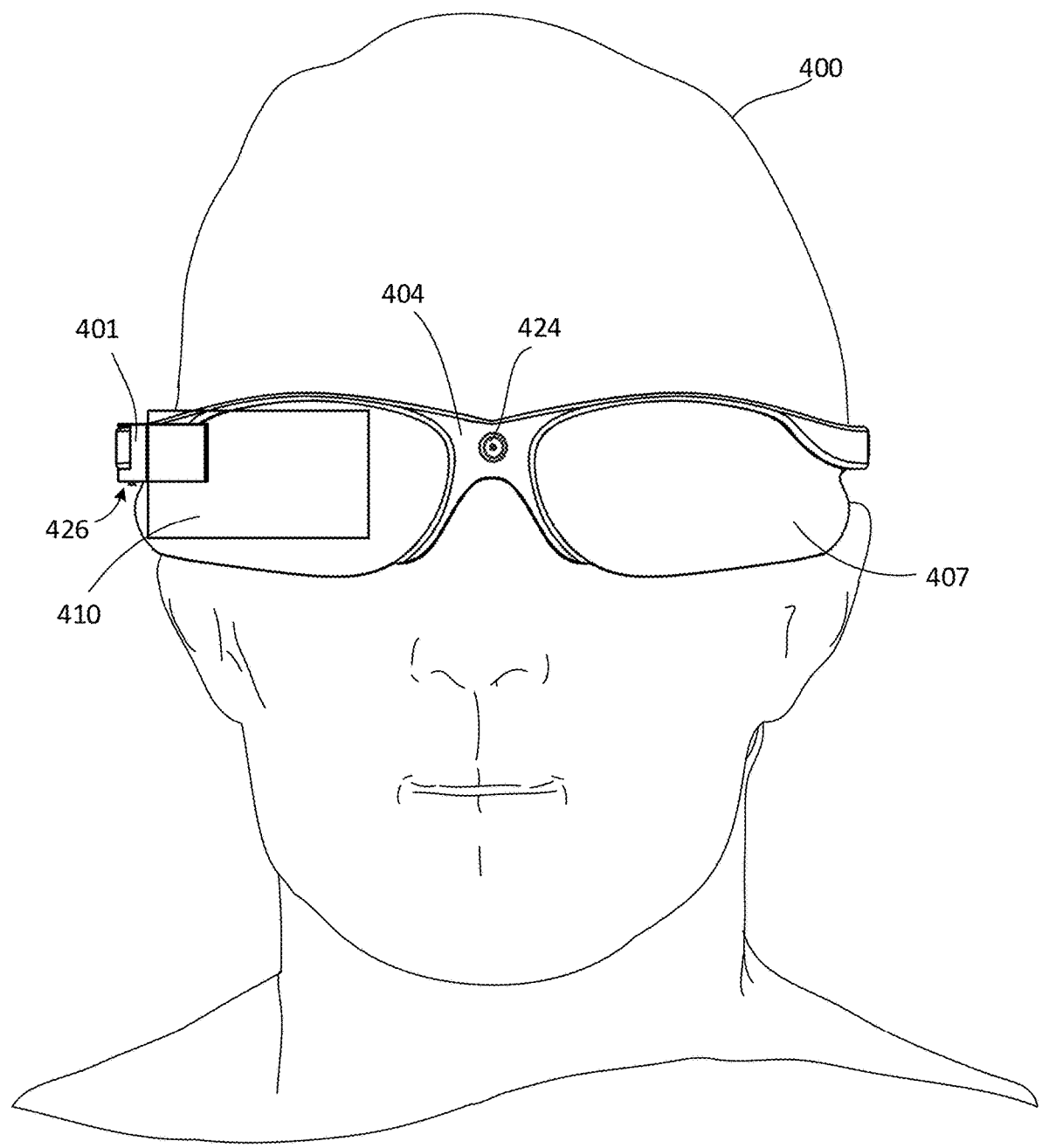
FIG. 4B illustrates an embodiment of the augmented display system of FIG. 4A equipped by a user.
Figure 4C:
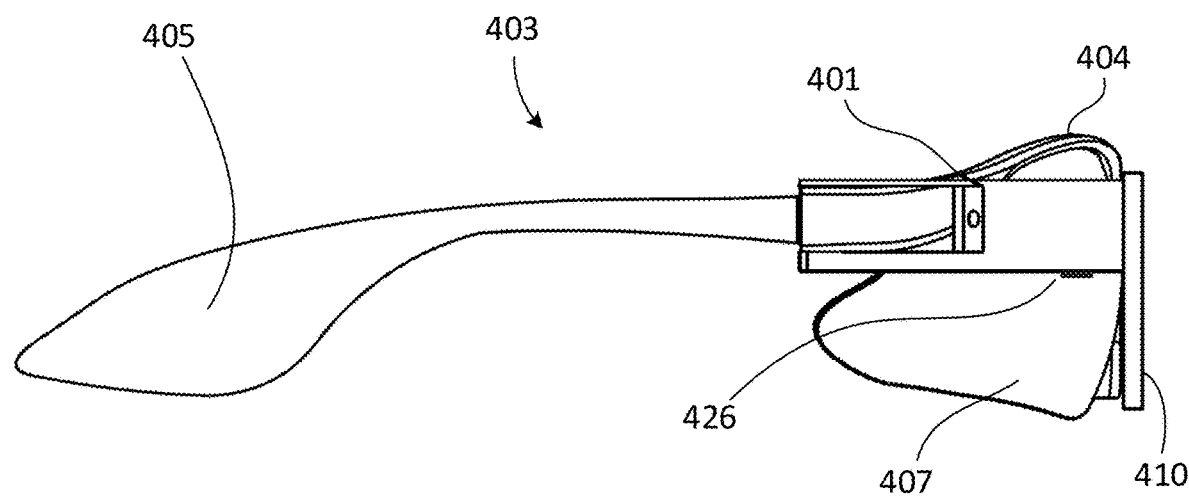
FIG. 4C depicts a side view of the embodiment of the augmented display system of FIG. 4*a*.

Referring to the drawings, FIGS. 4A-4C depict different views (i.e., perspective view, front view, and side view, respectively) of an embodiment of an augmented reality display system 403 which may be worn by a user 400 (see, FIG. 4B). As shown in the Figures, an embodiment of the augmented reality display system 403 includes a housing 401, a pair of glasses comprising a frame 404, a pair of arms 405 each comprising a hinge and a pair of lenses 407, a display device 410, a visual recognition system 424, and an audio recording system 426. The frame 404, arms 405 and lenses may be constructed out of any material known by a person skilled in the art of glasses construction. For example, the underlying components of the glasses of the augmented reality display system 403 may be constructed out of various plastics, resins, rubbers, metals or metal alloys, etc. While the exemplary embodiment of the augmented reality display system 403 is depicted as glasses, this should in no way be limiting to the appearance that the augmented reality display system 403 may take. Glasses are merely one example, and the augmented reality display system 403 may take other forms that comprise: a computer system capable of overlaying images or video data projected by the computer system onto a display device 410 having a HUD and GUI overlaid onto an object, or a digital representation of an object, where the object is being viewed in real time by a visual recognition system 424. A mobile device or tablet computer are other examples of an augmented display system 403 having a display device 410, a visual recognition system 424, and an audio recording system 426 as shown.

In an embodiment of the glasses that are used as an augmented reality display system 403, the system includes electrical and computing components integrated into the glasses themselves. For example, a projection device can be installed within the housing 401 attached to the frame 404 or arms 405 of the augmented reality display system 403 as shown in FIGS. 4A-4C. In an embodiment, within the interior of the housing 401, the computer system components integrated therein include any of the components described above for the augmented reality display system 403 and may also integrate other components of a generic computer system including processors, memory devices, input devices and output devices.

Figure 5:
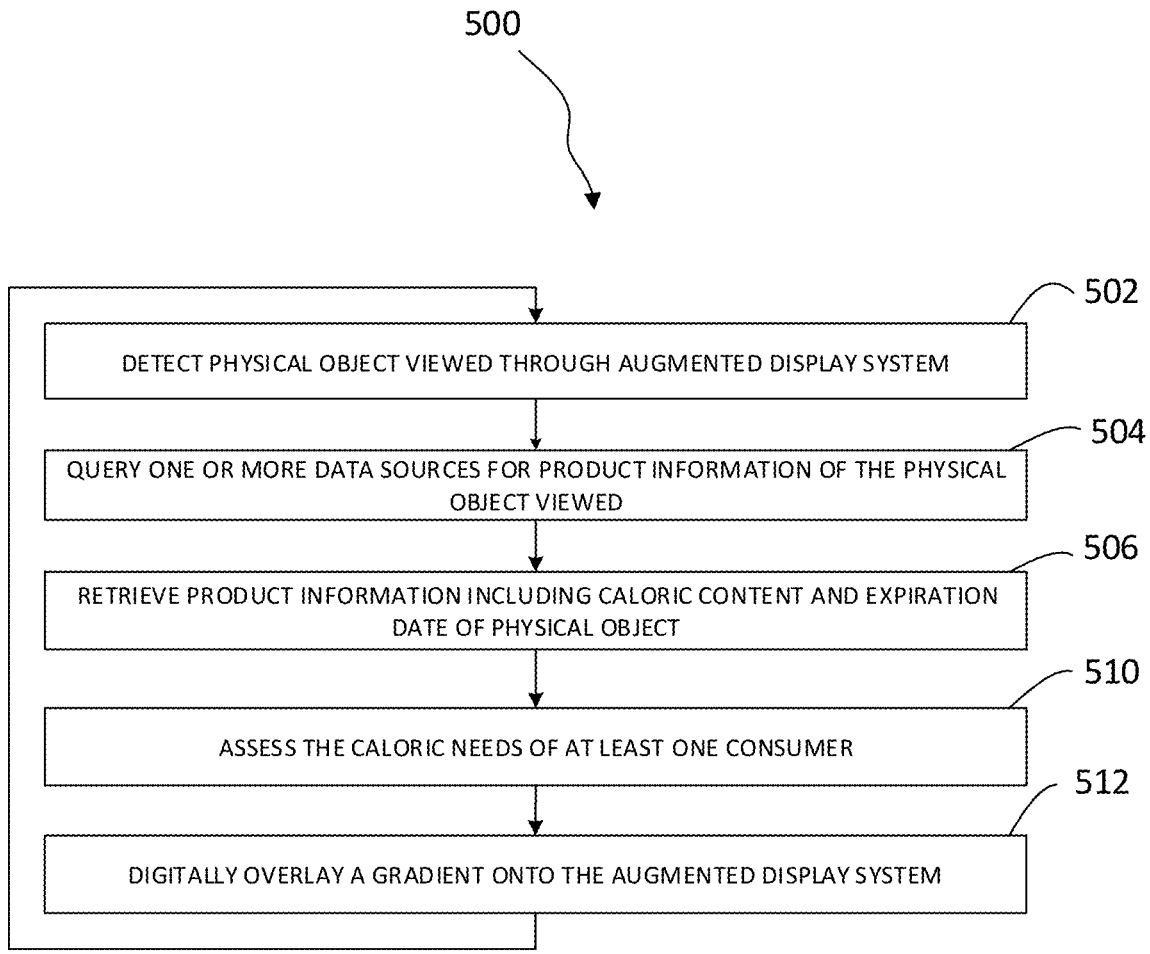
FIG. 5 is a flow chart of a method of an embodiment of an augmented display system.

FIG. 5 represents an embodiment of an algorithm 500 that is implemented for presenting a digital overlay to a user 400 using augmented reality, in accordance with the systems described in FIGS. 1-4C using one or more computer systems defined generically in FIG. 1. It should be appreciated that the steps of the method described in FIG. 5 may not require all the steps disclosed herein to be performed, nor does the algorithm of FIG. 5 necessarily require that all the steps be performed in the particular order presented. Variations of the method steps presented in FIG. 5 may be performed in a different order than that which is presented in FIG. 5.

The algorithm 500 described in FIG. 5 describes an embodiment of an algorithm for presenting a digital overlay to a user 400 using an augmented reality display system 403. The algorithm 500 initiates in step 502 by detecting the presence of a physical object 600 (see, FIG. 6) being viewed through visual recognition system 424 of the augmented reality display system 403. Detection of the object 600 may be performed using one or more object recognition techniques described above, by tracking the eye gaze of the user 400, or by allowing the user to manually identify when viewing an object of interest to the user. A visual recognition system 424 (see, FIGS. 4A-4C) identifies the type of physical object 600 (see, FIG. 6), and assigns a category, keywords or corresponding meta tags to the type of object. In one embodiment, the visual recognition system 424 captures an image of a bar code 626 (see, FIG. 6) associated with a physical object 600 (see, FIG. 6) and causes the bar code image to be processed to identify the physical object (e.g., a consumable food product). In other embodiments, the visual recognition system 424 captures one or more additional visual features (e.g., a product logo, a list of food ingredients, or an overall image of the object) of the physical object 600 to determine the identity.

In step 504, the visual recognition system 424 (see, FIG. 4A) initiates a query of one or more of the first storage device 122 and the second storage device 124 (see, FIG. 1) to retrieve product information 624 associated with the object 600 detected in step 502. It should be appreciated that in step 504, the query for product information 624 or other data associated with physical object 600 can be from any suitable number of storage devices, or other product information data sources that are stored locally, or across a network. The network may be a local area network (LAN), home area network (HAN), wide area network (WAN), back bone network (BBN), peer to peer network (P2P), campus network, enterprise network, the Internet, cloud computing network, and any other network or combination of networks known by a person skilled in the art.

In step 506, the visual recognition system 424 (see, FIG. 4A) retrieves, based on the query, product information 624 for the physical object 600. In certain examples, the product is a food product, and the product information 624 includes at least one of a list of ingredients, nutritional information, a caloric content, and an expiration date (e.g., a date by which something should no longer be used, either by operation of law or by exceeding an anticipated shelf life of a perishable good) of the food product.

In step 510, the algorithm 500 assesses the expected consumption of at least one consumer (e.g., user 400). In certain embodiments, the expected consumption is based on one or more of: past consumption data of one or more consumers, estimated caloric needs of one or more consumers, a current inventory of consumable products (i.e., how much consumables are currently in the possession of the consumers), the type of consumable product, and the nutritional content of the consumable product. In one example, the caloric needs of a consumer can be determined by biological data such as age, weight, height, metabolic rates, and any other suitable biological information. However, the biological needs of a consumer may differ from past consumption habits, and this information can be considered together to determine an expected consumption amount. In another example, past consumption data can be used alone to determine expected consumptions amounts, without regard to any biological data. In another example, the type of food, and the current inventory of food can be used to determine an expected consumption. For instance, if the consumer already has a large inventory of apples, and the type of consumable product being viewed through the augmented reality system 403 is also an apple, the algorithm 500 may determine that there is lower likelihood of consumption of further apples given that the current inventory is high. The algorithm 500 may use any combination of the above factors, or additional factors, to determine an expected consumption amount.

In step 512, the algorithm 500 compares the expected consumption of the consumers to determine a likely date by which the consumers will have consumed the product (i.e., the used by date). In step 512, the algorithm 500 compares the used by date to the expiration date of the product and determines whether the consumer is likely to have consumed all the product by the expiration date. In step 512, the algorithm 500 prepares a graphic overlay and presents this to the user 400 on a display device 410 (see, FIG. 4A) of the augmented reality system 403, the display device 410 including a HUD and GUI overlaid onto the object 401. As the position being viewed through visual recognition system 424 of the augmented reality display system 403 changes, other physical objects 600 may come into the viewing area of the visual recognition system 424. As the focus of the viewing area changes from one physical object 600 to another, the algorithm 500 proceeds from step 512 back to step 502, as shown in FIG. 5. This process can be repeated any number of times as the user 400 moves to different locations and/or changes the viewing angle of the augmented reality display system 403.

Figure 6:
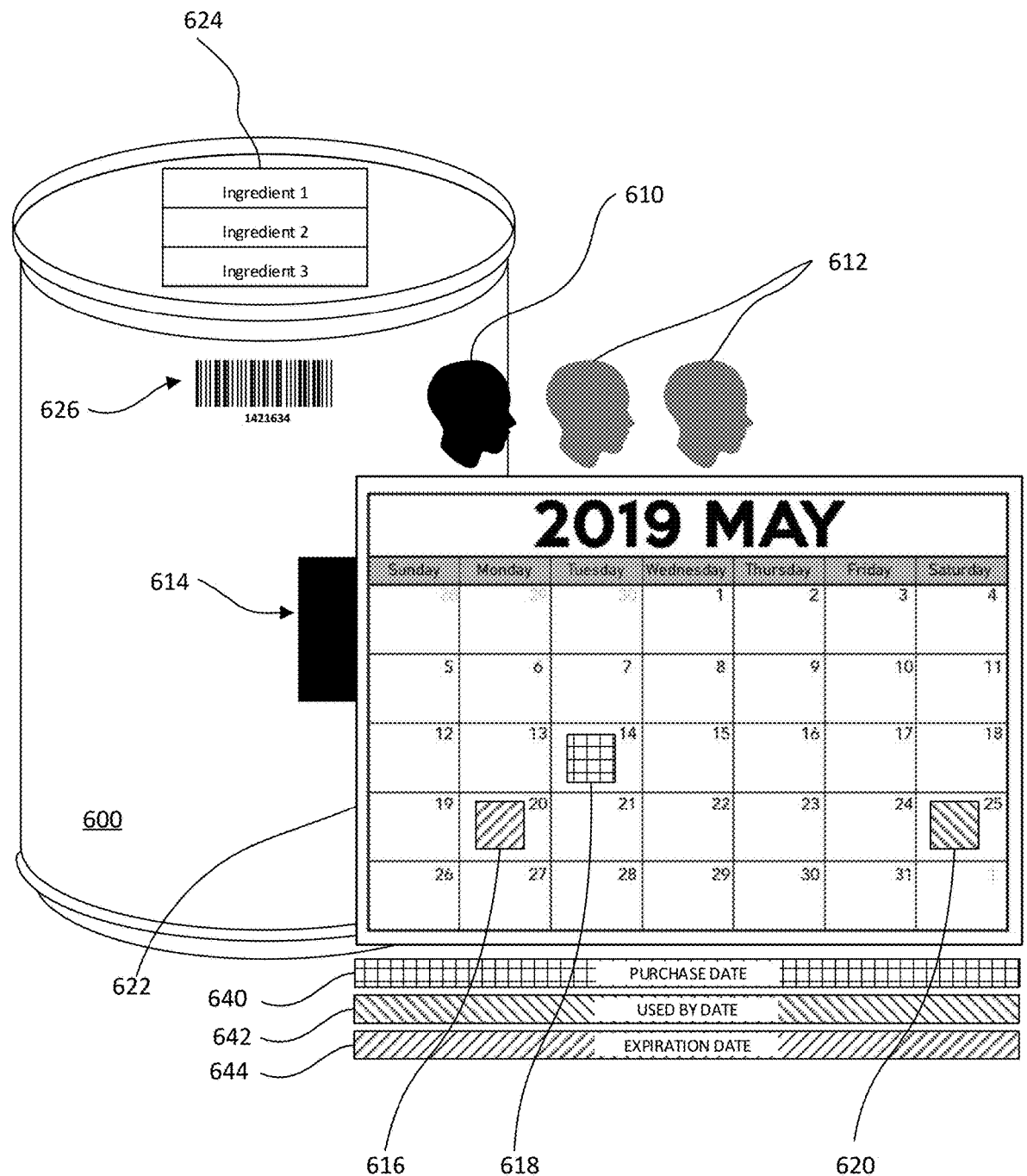
FIG. 6 illustrates an example of an augmented reality view of an overlay of a calendar depicting a purchase date, an expected used by date, and an expiration date of a physical object, in accordance with an embodiment.

Referring to the drawings, FIG. 6 illustrates an example of an augmented reality view of an overlay of a calendar 622 depicting a purchase date 640 (and a marking 618 of the purchase date), an expected used by date 642 (and a marking 620 of the expected used by date), and an expiration date 644 (and a marking 616 of the expiration date) of a physical object 600, according to an embodiment. The augmented reality display system 403 detects the presence of the physical object 600 being viewed through visual recognition system 424. Detection of the object 600 may be performed using one or more object recognition techniques described above. The visual recognition system 424 (see, FIG. 4A-4C) identifies the type of object 600, and assigns a category, keywords or corresponding meta tags to the type of object. In one embodiment, the visual recognition system 424 captures an image of the bar code 626 (or QR code, or any other suitable product identifying features) associated with a physical object 600 and causes the bar code image to be processed to identify the physical object (e.g., a consumable food product). In other embodiments, the visual recognition system 424 captures one or more additional visual features (e.g., a product logo, a list of food ingredients, product information 624, or an overall image of the object) of the physical object 600 to determine the identity.

As shown in FIG. 6, in an embodiment, the augmented reality display system 403 presents an overlay of a calendar 622 to the user 400. The calendar 622 includes markings (e.g., 616, 618 and 620) that are representative of different dates associated with the physical object 600. In this example of FIG. 6, the markings are square/rectangular shapes that fit within a space occupied by a day of the month. However, it should be appreciated that the markings may be any other suitable visual features or text that differentiate between the different date categories (e.g., purchase date). In this example, marking 618 represents a purchase date of the product. Generally, this would correspond with the same day that the user 400 is presently viewing the physical object. Marking 616 represents an expiration date of the physical object 600 and marking 620 represents an expected used by date of the object. As described above, the expiration date of the physical object 600 is an estimated date that the product will no longer be suitable for human consumption, or more generally a date beyond which it is recommended for consumption. The used by date 642 is the date that the algorithm 500 of the augmented reality display system 403 has determined to be a likely date by which the consumers will have fully consumed the product.

This used by date 642 may be based on the number of consumers that will be consuming the product, and/or the determined caloric needs of the consumers. In the example shown in FIG. 6, there is only one consumer 610 indicated by black shading. However, there may be any other suitable number of consumers 612, as indicated by gray shading. Consumers 610 and 612 form a consumer group (e.g., a household). In one embodiment, as shown in FIG. 6, the visual overlay presented to the user 400 also includes a rectangular marker 614 that indicates a direction or location of the physical object 600 relative to the calendar. In one example, the position of the marker 614 is adjacent to the left side of the calendar 622 and is in a vertical position on the left side of the calendar 622. In one example, the vertical position of the marker 614 at least approximately corresponds to a position of a two-dimensional center of mass of the physical object 600. For example, if the physical object 600 were positioned lower in the field of view, the position of the marker 614 would appear further to the bottom of the left side of the calendar 622. In another example where there is only one physical object in the field of view of the visual recognition system 424, the marker 614 would not move relative to the calendar 622, but the combination of the marker 614 and the calendar 622 would move relative to the change in position of the physical object 600. In this example, the position of the combined overlay (e.g., 610, 612, 614, 616, 618, 620, 622, 640, 642, 644) would move to track the changing position of the physical object 600 in the field of view of the visual recognition system 424.

In one embodiment, as shown in FIG. 6, the overlay also includes a legend that includes textual display elements for the purchase date 640, the used by date 642, and the expiration date 644. The legend for the purchase date 640 corresponds to the display feature 618 on the calendar 622, the legend for the used by date 642 corresponds to the display features 620 on the calendar 622, and the legend for the expiration date 644 corresponds to the display feature or marking 616 on the calendar 622. In this example, because the expiration date (i.e., May 20) is earlier than the calculated used by date (i.e., May 25), there is a concern that the caloric content of the physical object 600 exceeds the caloric needs of the user 400 in the time between the purchase date and the expiration date. In other words, there is a concern that food will be wasted because the consumer will not likely consume all the food before the expiration date.

Figure 7:
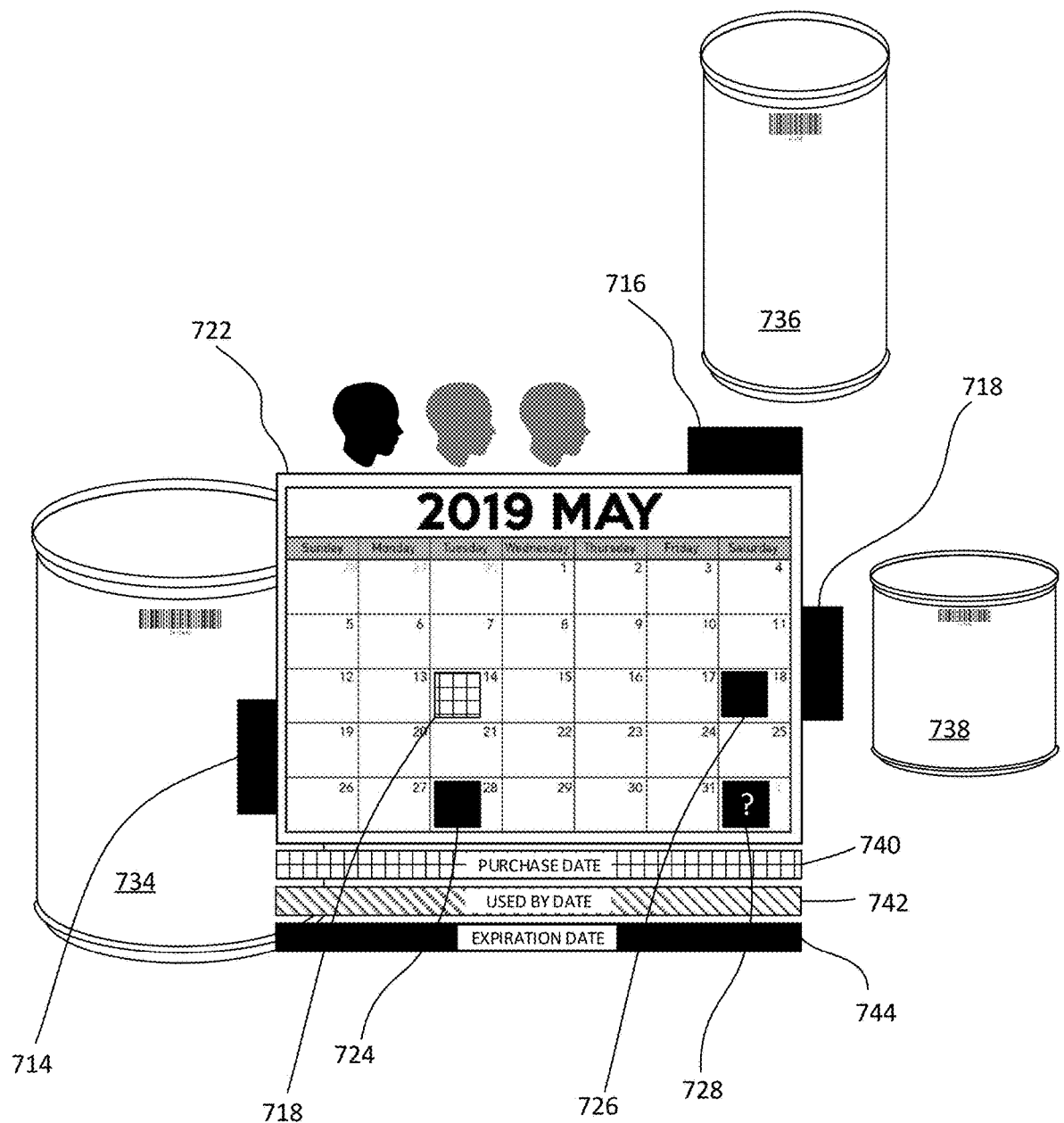
FIG. 7 depicts an illustrative example of an augmented reality view of an overlay of a calendar depicting expiration dates of multiple physical objects, in accordance with an embodiment.

As shown in FIG. 7, in an embodiment, the augmented reality display system 403 presents an overlay of a calendar 722 to the user 400. In this example, there are multiple physical objects 734, 736 and 738 in the field of view of the of the visual recognition system 424. In this embodiment, the visual overlay presented to the user 400 also includes multiple rectangular markers 714, 716 and 718 that indicate directions and/or locations of the physical objects 734, 736 and 738, respectively. In this example, the position of the marker 714 is adjacent to the left side of the calendar 722 and is in a lower central vertical position on the left side of the calendar that at least approximately corresponds to a position of a center of mass of the physical object 734. Also, the position of the marker 716 is adjacent to the top side of the calendar 722 and is in a rightward horizontal position on the top side of the calendar that at least approximately corresponds to a position of a center of mass of the physical object 736. Moreover, the position of the marker 718 is adjacent to the right side of the calendar 722 and is in an upper central vertical position on the right side of the calendar that at least approximately corresponds to a position of a center of mass of the physical object 738. In the example shown in FIG. 7, where there are multiple physical objects in the field of view, the calendar 722 only shows the purchase date 740, and the expiration dates 724, 726 and 728. However, it should be appreciated that the calendar overlay could alternatively show any combination of the purchase date, the expiration dates, and the used by dates for one or more of the products. For example, the markers 714, 716 and 718 could each be displayed as a different colored rectangle, and for a given marker and color, each of the purchase date, used by date, and expiration date could have corresponding display features on the calendar in the respective color. As such, there would be several different expiration date features and used by date features displayed on the same calendar 622. In the embodiment shown in FIG. 7, the overlay also includes a legend that includes textual display elements for the purchase date 740, the used by date 742, and the expiration date 744.

As also shown in FIG. 7, the expiration date 728 is indicated as a question mark. In one example, this indicates that the augmented reality display system 403 was unable to determine an expiration date for the product. Alternatively, this could mean that the product has a very long shelf life (e.g., rice or canned goods), and the expiration date is far off into the future. In an alternative embodiment, if the expiration date was in a month (e.g., June or July) that was after the current calendar month (e.g., May) being viewed, the marker 728 could indicate an arrow or some other suitable feature to indicate to the user that the information regarding the expiration date of that particular product is in a future month. In this situation, in an embodiment, the user could scroll ahead in time to view calendars for future months. Alternatively, the augmented reality display system 403 could dynamically adjust the overlay display to the user to accommodate for a plurality of months of data, as necessary.

Figure 8:
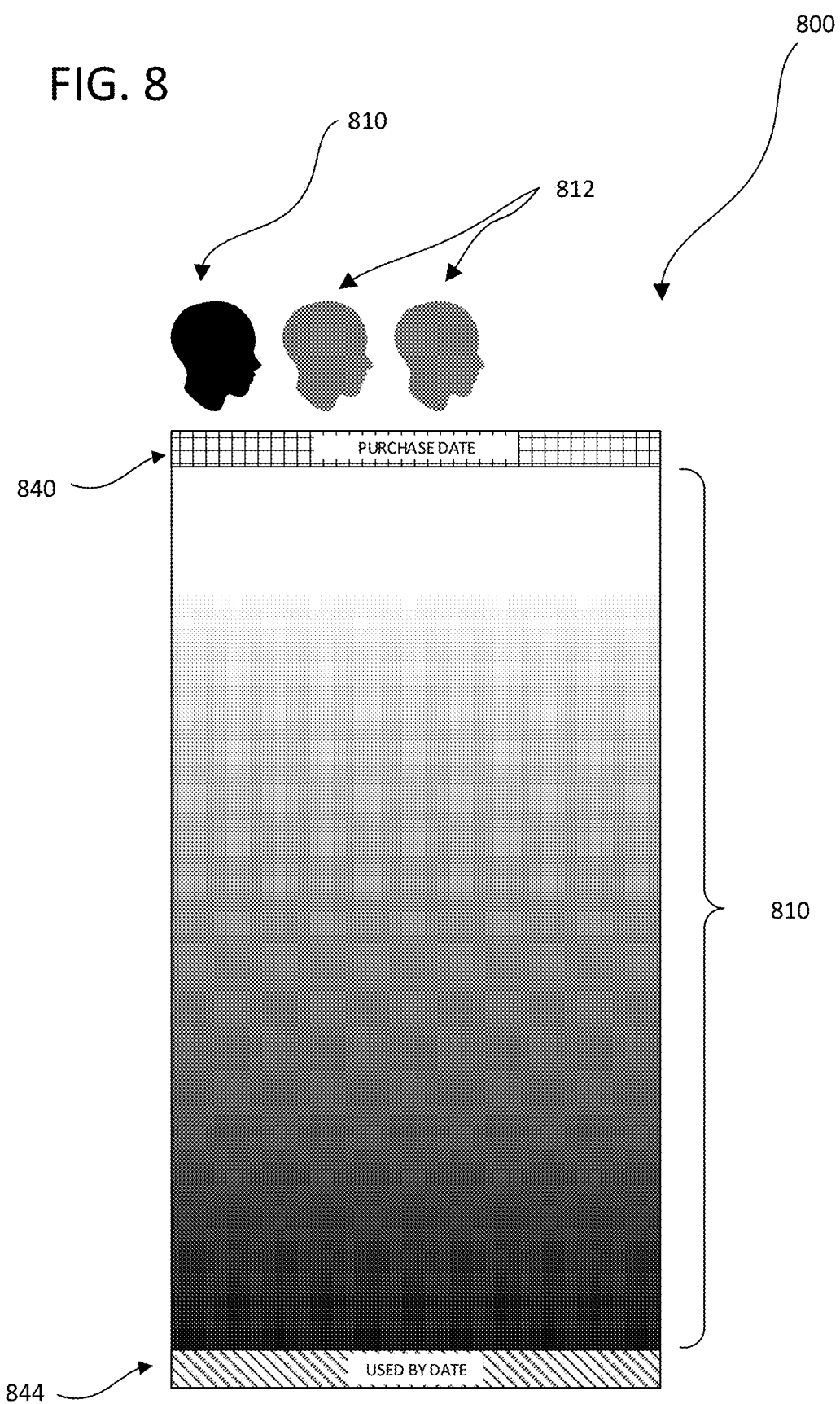
FIG. 8 depicts an illustrative example of an augmented reality view of a gradient overlay depicting a purchase date, an expected used by date, and a color gradient indicating a likelihood that a physical object will reach an expiration date prior to the expected used by date, in accordance with an embodiment.

As shown in FIG. 8, in an embodiment, the augmented reality display system 403 presents a visual overlay 800 to the user 400, where the visual overlay includes a purchase date 840, a used by date 844, and a gradient 810. In the example shown in FIGS. 8 and 9, the gradient 810 is an image gradient that is a directional change in the intensity or color in an image, where the intensity in color is darkest at the bottom and gets lighter toward the top. However, it should be appreciated that the gradient could be any suitable visual indication of a likelihood that a used by date 844 of a physical object would exceed the expiration date of the object. That is, the gradient could be any suitable graphical indication that would visually alert the user 810, 812 to the extent or magnitude of a risk of spoilage of a consumable product. For example, the gradient could be a variable crosshatching pattern, or variable stippling (i.e., creation of a pattern simulating varying degrees of solidity or shading by using small dots or other repetitively used shapes).

In an embodiment, the vertical distance of the gradient 810 represents an amount of time (e.g., two weeks). In an embodiment, the rate of change of the gradient 810 in the vertical direction is constant. However, in another embodiment, the rate of change of the gradient 810 in the vertical direction is not constant. For example, in this other embodiment, if the product is one that is determined to spoil rapidly and relatively precisely at the expiration date (e.g., bananas, avocados or some other perishable produce product), the gradient may accelerate rapidly toward the darker color right at the expiration date (i.e., indicating a rapid increase in the probability of spoilage). However, for a product with a longer shelf life (i.e., a product like dry rice with a lower expectation of immediate spoilage after the expiration date), the gradient may change very slowly toward the darker color at the expiration date.

Figure 9:
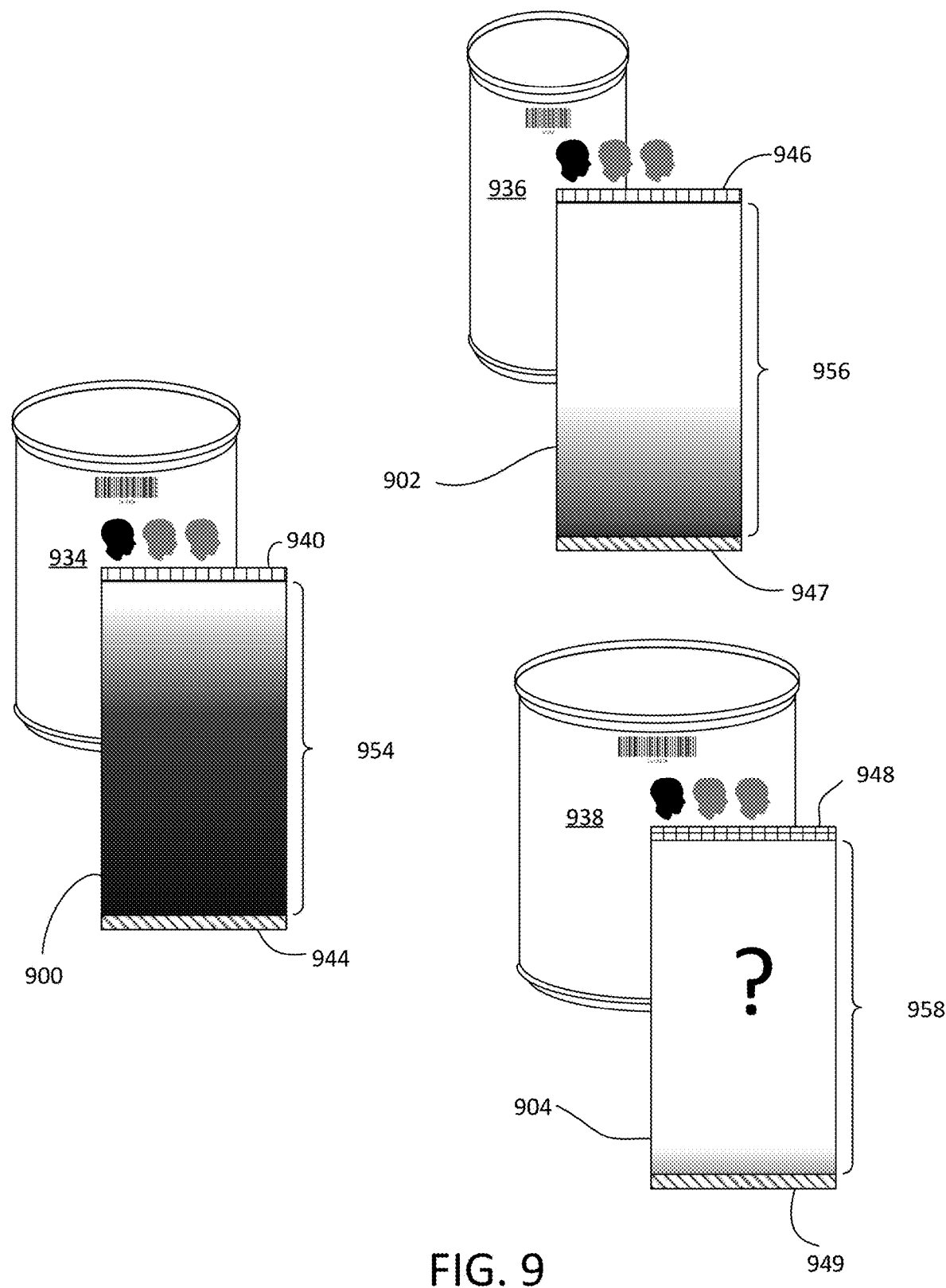
FIG. 9 depicts an illustrative example of an augmented reality view of multiple gradients depicting respective purchase dates, expected used by dates, and color gradients indicating likelihoods that different physical objects will reach their respective expiration dates prior to the respective expected used by dates, in accordance with an embodiment.

As shown in FIG. 9, in an embodiment, the augmented reality display system 403 presents visual overlays 900, 902 and 904 to the user 400, where the visual overlays include a plurality of different gradients 954, 956 and 958, respectively. Like the embodiment shown in FIG. 7, the embodiment shown in FIG. 9 has three different physical objects 934, 936 and 938. However, FIG. 9 is different in that instead of showing a calendar overlaying the object, there are a plurality of gradients overlaying the objects.

Regarding physical object 934, this product has a purchase date of May 14, an expiration date of May 20, and a used by date of May 28. Because the expected used by date (May 28) of physical object 934 far exceeds the expiration date (May 20), there is high likelihood that the product will spoil before the user 400 consumes it all. Thus, the gradient 954 shows a very intense dark color extending from bottom to the top, which alerts the user that there is a high risk of spoilage. Regarding physical object 936, this product has a purchase date of May 14, an expiration date of May 29, and a used by date of May 19. Because the expiration date (May 29) of physical object 936 exceeds the used by date (May 19), there is a low likelihood that the product will spoil before the user 400 consumes it all. Thus, the gradient 956 shows a very relatively lighter color (when compared to gradient 954) extending from bottom to the top, indicating to the user that there is very low risk of spoilage. Finally, regarding physical object 938, this product has a purchase date of May 14, an expiration date of December 31, and a used by date of May 23. Because the expiration date (December 31) of physical object 938 far exceeds the used by date (May 23), there is a very low likelihood that the product will spoil before the user 400 consumes it all. In this example, the physical object 936 is a product with a very long shelf life. Thus, the gradient 958 shows a much lighter color range (when compared to both gradient 954 and gradient 956) extending from the bottom to the top. Thus, the user 400 can view multiple products and see multiple gradients, and easily understand by the strength/intensity of the gradients which of these products will be likely to spoil before complete consumption. Thus, at the time of purchase of the products, the user is readily able to determine possible food waste, and make informed decisions regarding whether to purchase certain items.

In one embodiment, the augmented reality display system 403 (see e.g., FIGS. 4A-4C) enables a user to input data regarding whether food was spoiled, or regarding an amount of spoilage. The augmented reality display system 403 causes this data to be stored to at least one storage device 122 or 124 (see, FIG. 1). The augmented reality display system 403 can thus store and track spoilage rates and provide feedback to the user through the augmented reality display system 403 regarding same. Thus, a user can determine success or failure trends regarding food spoilage.

In one embodiment, the augmented reality display system 403 enables a user to select one or more consumers (see e.g., consumer 610 and multiple other consumers 612 of FIG. 6), and specify caloric intake needs (or other biological information such as age, weight, height, metabolic rates, etc.) of each user to determine total caloric needs for the group (e.g., a household).

In another embodiment, the augmented reality display system 403 calculates an estimated next shopping date based on at least one of user habits, history of caloric consumption, historical amounts of food wasted, and data regarding the expiration dates and used by dates of previously purchased products. In an example, if the user has not consumed all the products (i.e., the used by dates are far off in the future), but the expiration dates of all the products are approaching, the augmented reality display system 403 can determine that most of the food will be expiring (i.e., possible spoilage) soon (regardless of consumption), and offer an estimated next shopping date based on the expiration dates. In another example, when the expiration dates of all the products are far off in the future, but the used by dates are approaching, the augmented reality display system 403 determines that the estimated next shopping date should be in the near future and should correspond to a certain degree with the various used by dates. The estimated next shopping date can be based on both the expiration dates and the used by dates of a plurality of physical objects. In another embodiment, the augmented reality display system 403 displays indications on the calendar 622 overlay regarding previous shopping trips or previous food purchases.

In an embodiment, the augmented reality display system 403 provides alerts to the user 400 that previously purchased food is approaching an expiration date, thus enabling the user to make informed decisions regarding which food to consume, and in what order, to potentially minimize waste. In another embodiment, the augmented reality display system 403 provides alerts to the user regarding the monetary costs of previously wasted food, or costs of food that will likely be wasted in the future.

In an embodiment, the augmented reality display system 403 determines the ingredients that are associated with a physical object and presents alternative ingredient options to a user that may better suit the present caloric needs of the user 400 or group of users. For example, if the augmented reality display system 403 detects the presence of a physical object 600 with a very high caloric density or content (where possibly the caloric content exceeds the estimated caloric needs of the users), the augmented reality display system 403 can offer alternative suggestions for a different food product that may have certain palatable similarities but with a lower caloric content (e.g., suggest a low calorie spinach salad as a substitute for a higher calorie tuna and mayonnaise salad). In this way, in the event of a potential caloric excess at the time of purchase, the user can consider alternative food choices that may lead to reduced waste.

In an embodiment, the augmented reality display system 403 associates the food type of a physical object 600 with a portion. The portion is assigned a relative amount of consumption (i.e., expected individual verse expected recommended) based on Food and Drug Administration guidance.

In an embodiment, based on caloric consumption needs of a user, and based on caloric content of a product, the augmented reality component 170 determines a likely amount of consumption (e.g., ½, ⅓, ¼) over a particular time frame (one day, one week, one work week, one month), and presents this information to the user 400 on an overlay via the augmented reality display system 403. In another embodiment, the augmented reality display system 403 presents information to the user regarding the number of meals that the user is likely to consume for a particular physical product.

In an embodiment, a user can select the number of consumers in a household. In this embodiment, if the user selects a different number of consumers, the system recomputes the caloric consumption needs of the group of consumers and adjust the expected used by dates according the increased caloric needs of the group. For example, if the user increases the number of consumers, the used by date for a particular product would be sooner because it is calculated that the larger group would consume the product faster.

In an embodiment, rather than presenting a gradient to the user, the system presents textual information to the user on the augmented reality display device regarding a likelihood of waste of the consumable products. For example, the information to the user could be a warning to the consumer to not buy the product as there is a high likelihood of waste. In another embodiment, rather than presenting a gradient or textual information to the user, the system presents a visual cue as to whether the user should buy the product (e.g., a green button to buy, or a red button not to buy).

In an embodiment, a vertical size of the gradient changes depending a length of time between the purchase date of the product, and the expects use by dates.

In a situation where many products are viewed through the visual recognition system of the augmented reality display system (e.g., in a shopping aisle of a grocery store with hundreds of products), there is a concern that the viewing area of the augmented reality display system could get very crowded with the visual overlays. In an embodiment, to minimize potential crowding of visual information, the displayed results are filtered to show only a subset of the products (e.g., those products that have a high likelihood of spoilage or waste, or products with a low likelihood of spoilage or waste). For example, if there were ten products being viewed at the same time, and one of the products was a tuna salad with a short expiration date and the user has low caloric needs (i.e., high likelihood of waste), the augmented reality display system would not cause a gradient overlay of the tuna salad to be presented to the user.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   detecting an object being viewed through a visual recognition system, the object having an associated expiration date;
   determining a caloric content associated with the object;
   assessing caloric consumption needs of at least one consumer;
   determining a likelihood of consumption of the object by the consumer based on the caloric content of the object, the caloric consumption needs of the consumer, and the expiration date of the object; and
   displaying a gradient on a display device as an overlay associated with the object, the gradient representing a changing likelihood of total consumption of the object by the consumer over a period of time.

2. The method of claim 1, wherein the gradient is an image gradient having a directional change in an intensity or a color of the image, and a dimension of the gradient represents the period of time.

3. The method of claim 1, further comprising determining a used by date for the object, the used by date representing the date that consumer is expected to have consumed the object, wherein the used by date is based on the caloric content of the object and the caloric consumption needs of the consumer.

4. The method of claim 3, wherein the period of time begins at a purchase date of the object, and ends at the used by date of the object.

5. The method of claim 4, wherein the gradient is an image gradient having a directional change in an intensity or a color of the image, and a dimension of the gradient represents the period of time.

6. The method of claim 1, wherein the assessment of the caloric consumption needs is based on at least one biological factor of the consumer.

7. The method of claim 1, further comprising:
   determining a number of consumable portions associated with the object;

determining used by dates that the consumable portions would likely be consumed by the at least one consumer; and displaying representations of these dates on the display device.

8. The method of claim 7, further comprising displaying on the display device representations of whether the used by dates of the consumable portions extend beyond the expiration date of the object.

9. The method of claim 1, wherein the method includes displaying a plurality of different gradients on the display device, each of the gradients being associated with one of a plurality of different objects detected by the visual recognition system.

10. The method of claim 9, wherein the gradients are image gradients each having a directional change in an intensity or a color of the image, and a dimension of each of the gradients represents the period of time, and at least a first one of the gradients is different than a second one of the gradients.

11. The method of claim 1, wherein a rate of change of the gradient is not constant, and is based on a type of the object.

12. A computer system comprising:
  a computer readable storage medium with program instructions stored thereon; and
  one or more processors configured to execute the program instructions to perform a method comprising:
  detecting, by the processors, an object being viewed through a visual recognition system, the object having an associated expiration date;
  determining, by the processors, a caloric content associated with the object;
  assessing, by the processors, caloric consumption needs of at least one consumer;
  determining, by the processors, a likelihood of consumption of the object by the consumer based on the caloric content of the object, the caloric consumption needs of the consumer, and the expiration date of the object; and
  causing, by the processors, a gradient to be displayed on a display device as an overlay associated with the object, the gradient representing a changing likelihood of total consumption of the object by the consumer over a period of time.

13. The computer system of claim 12, wherein the gradient is an image gradient having a directional change in the intensity or the color of the image over the period of time.

14. The computer system of claim 12, further comprising determining a used by date for the object, the used by date representing a date that consumer is expected to have consumed all of the object, wherein the used by date is based on the caloric content of the object and the caloric consumption needs of the consumer.

15. The computer system of claim 14, wherein the period of time begins at a purchase date of the object, and ends at the used by date of the object.

16. The computer system of claim 12, wherein the method includes displaying a plurality of different gradients on the display device, each of the gradients being associated with one of a plurality of different objects detected by the visual recognition system.

17. The computer system of claim 16, wherein the gradients are image gradients each having a directional change in an intensity or a color of the image, and a dimension of each of the gradients represents the period of time, and at least a first one of the gradients is different than a second one of the gradients.

18. A computer program product for implementing a method for determining a likelihood of consumption of a product using augmented reality, the computer program product comprising a computer readable storage medium having program instructions embodied therewith, the program instructions executable by at least one computer processor to cause the computer processor to:
  detect, by the processor, an object being viewed through a visual recognition system, the object having an associated expiration date;
  determine, by the processor, a caloric content associated with the object;
  assess, by the processor, caloric consumption needs of at least one consumer;
  determine, by the processor, a likelihood of consumption of the object by the consumer based on the caloric content of the object, the caloric consumption needs of the consumer, and the expiration date of the object; and
  cause, by the processor, a gradient to be displayed on a display device as an overlay associated with the object, the gradient representing a changing likelihood of total consumption of the object by the consumer over a period of time.

19. The computer program product of claim 18, wherein the gradient is an image gradient having a directional change in the intensity or the color of the image over the period of time.

20. The computer program product of claim 18, wherein the program instructions are executable by the at least one computer processor to cause the computer processor to display a plurality of different gradients on the display device, each of the gradients being associated with one of a plurality of different objects detected by the visual recognition system.

* * * * *